United States Patent [19]

Characklis et al.

[11] Patent Number: 4,485,450
[45] Date of Patent: Nov. 27, 1984

[54] MONITORING BUILD-UP OF FOULING DEPOSITS ON SURFACES OF FLUID HANDLING SYSTEMS

[75] Inventors: William G. Characklis; Frank L. Roe, both of Bozeman, Mont.

[73] Assignee: Bridger Scientific, Inc., Bozeman, Mont.

[21] Appl. No.: 338,972

[22] Filed: Jan. 12, 1982

[51] Int. Cl.³ ............... G01N 11/14; G06F 15/46
[52] U.S. Cl. ................................. 364/550; 73/60
[58] Field of Search .............. 73/59, 60, 61.2; 364/509, 510, 508, 550

[56] References Cited

U.S. PATENT DOCUMENTS

| | | | |
|---|---|---|---|
| 3,875,791 | 4/1975 | Fitzgerald et al. | 73/59 |
| 4,077,252 | 3/1978 | Stutz et al. | 73/59 |
| 4,165,631 | 8/1979 | Boinet et al. | 73/59 X |
| 4,299,118 | 11/1981 | Gau et al. | 73/59 |
| 4,341,111 | 7/1982 | Husar | 73/59 X |
| 4,352,287 | 10/1982 | Orth et al. | 73/60 |
| 4,373,147 | 2/1983 | Carison, Jr. | 73/59 X |

Primary Examiner—Edward J. Wise
Attorney, Agent, or Firm—Eric P. Schellin

[57] ABSTRACT

An instrument for monitoring the build-up of fouling deposits on the liquid-handling surfaces of cooling towers, heat exchangers and other apparatus, subject to liquid fouling, is disclosed in this application. The build-up is monitored by sensing the increasing drag on a rotor immersed in the liquid, as the rotor and adjacent stationary surfaces become fouled. The drag is measured by a torque transducer, which is connected to read-out devices by means of a computer. The instrument may be used as an integral part of a feedback control system, or for evaluating fouling control strategies. The computer enables the instrument to operate in different modes, as desired.

5 Claims, 17 Drawing Figures

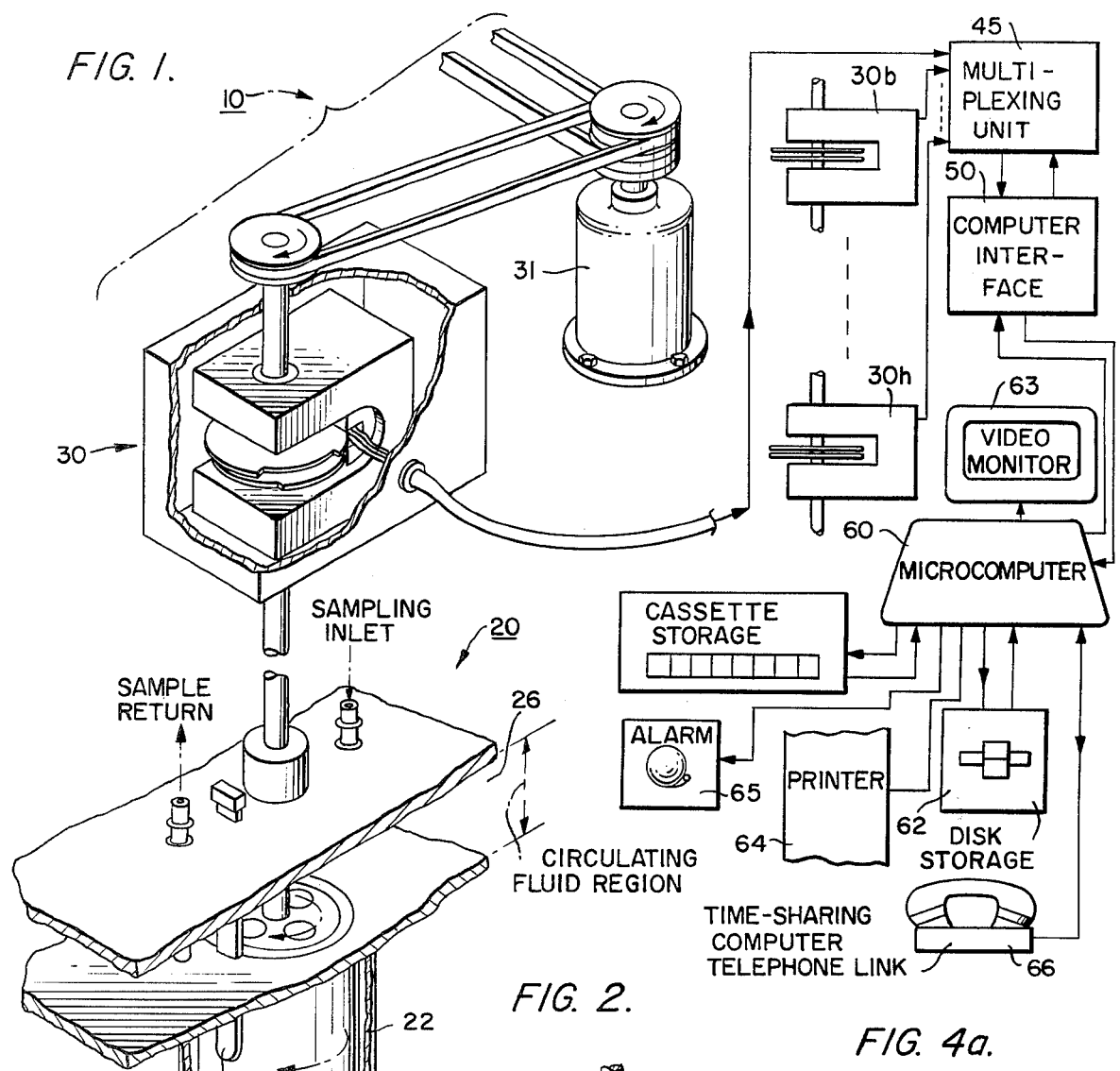

FIG. 5b.
FIG. 5a.
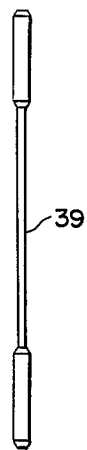
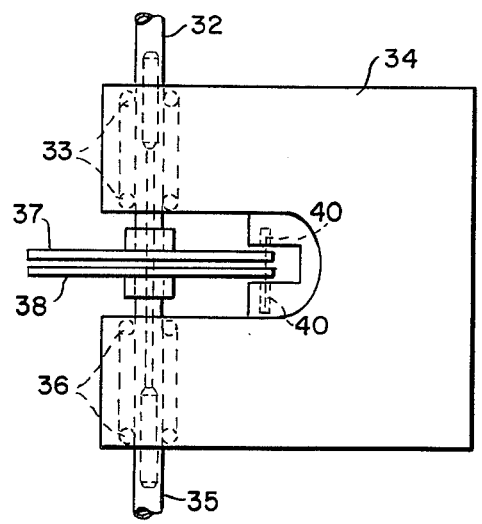
FIG. 6.
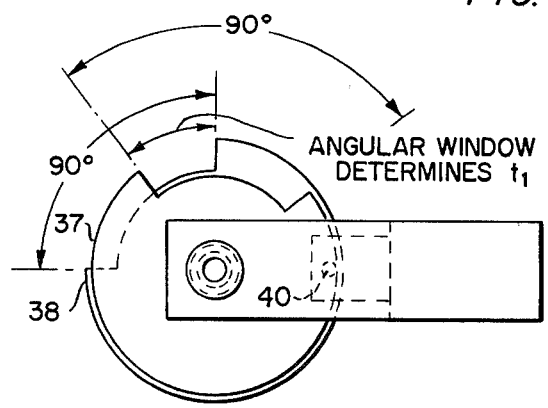
FIG. 7.
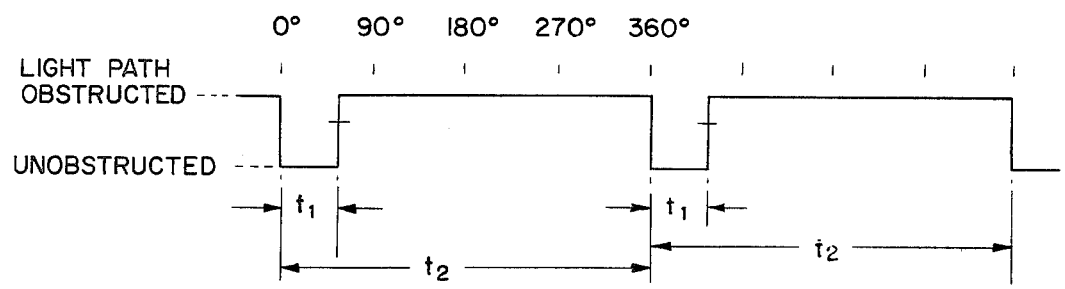

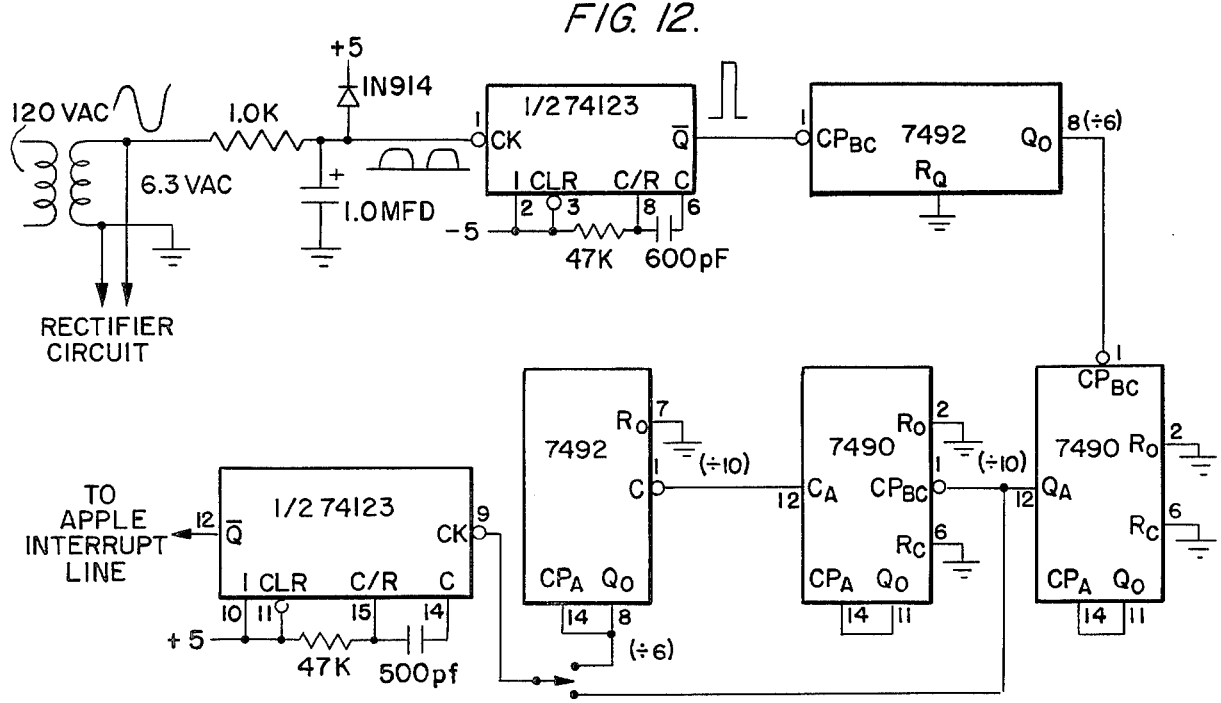
FIG. 12.
FIG. 13.
| IC | Vcc | GND |
|---|---|---|
| 74123 | 16 | 8 |
| 7492 | 5 | 10 |
| 7490 | 5 | 10 |
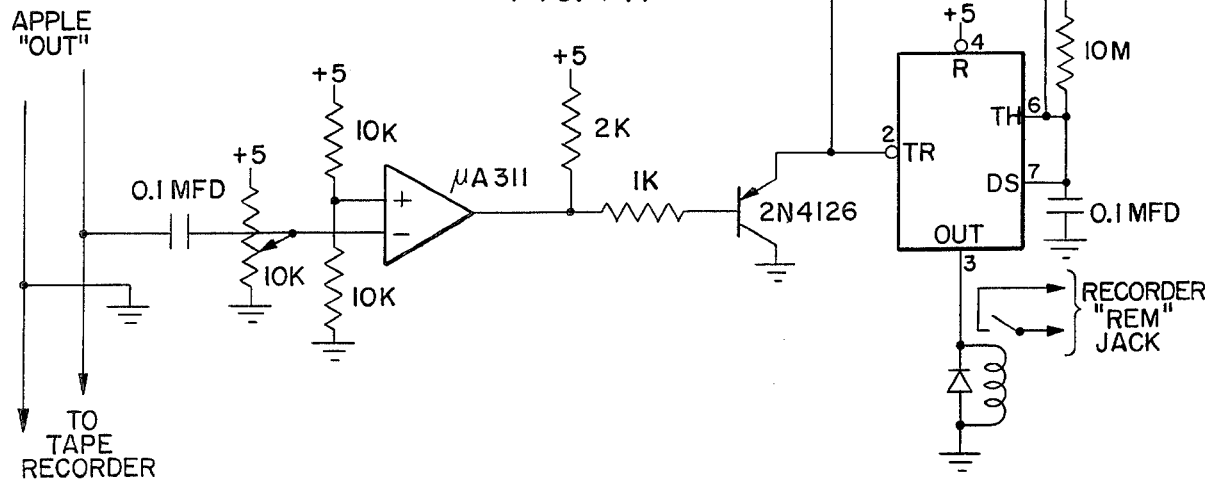
FIG. 14.
FIG. 15.
| IC | Vcc | GND |
|---|---|---|
| μA311 | 8 | 1 |
| 555 | 8 | 1 |

4,485,450

MONITORING BUILD-UP OF FOULING DEPOSITS ON SURFACES OF FLUID HANDLING SYSTEMS

SUMMARY

In many kinds of liquid handling systems, such as heat exchangers, the surfaces exposed to the liquid can become fouled with deposits to such an extent that the deposits interfere with proper operation. This is particularly true of cooling towers, in which aerated water cascades over the heat exchange surfaces. The build-up is largely biological, as by growth of adherent algae and slime, and may also be partly chemical, as by accretion of calcium deposits.

Monitoring of such fouling deposits is achieved by the herein disclosed system. It comprises an annular fouling cell in which a continuous and controlled flow of cooling water passes through a cylindrical casing in which a concentric rotor is driven. As the rotor surfaces and the adjacent casing surfaces become fouled, the drag on the rotor is increased in proportion to the fouling. This drag is sensed by a torque transducer located in the mechanical drive between an electric motor and the concentric rotor of the annular fouling cell.

The torque sensor emits a binary signal which is interpreted by a computer interface and central computer, to derive information on both the rotary velocity of and the torque required to drive the cylindrical rotor of the annular fouling reactor.

The data thusly collected is stored as digital information on inexpensive cassette tapes. Thus the tedious task, often error-prone, of manual transcription of data is eliminated. The information stored in the cassettes is adapted for further computer analysis, useful in devising control strategies for the expansion of the system for control applications, including automatic feedback control.

VIEWS OF DRAWING

FIG. 1 is a general view of the overall biological fouling monitor.

FIGS. 2 and 3 are, respectively, longitudinal and radial cross sectional views of the annular fouling reactor, as viewed on the sections 2—2 and 3—3, respectively.

FIGS. 4a and 4b are, respectively, top and side views of the removable slide.

FIGS. 5a and 5b are, respectively, views of the torque transducer and a torsional spring rod used therein.

FIG. 6 is a top view of the torque transducer.

FIG. 7 is a graph illustrating the operation of the sectored disks of the torque transducer.

FIG. 8 is a schematic of the torque transducer, multiplexing unit and computer interface while FIG. 9 is a table of bias voltages therefor.

FIG. 12 is a schematic of the clock-interrupt circuit used with the Apple microcomputer, while FIG. 13 is a table of bias voltages therefor FIG. 14 is a schematic of the interface between Apple computer and a tape recorder, enabling the computers output to be automatically recorded, while FIG. 15 is a table of bias voltages therefor.

DETAILED DESCRIPTION

Figures 8, 9:
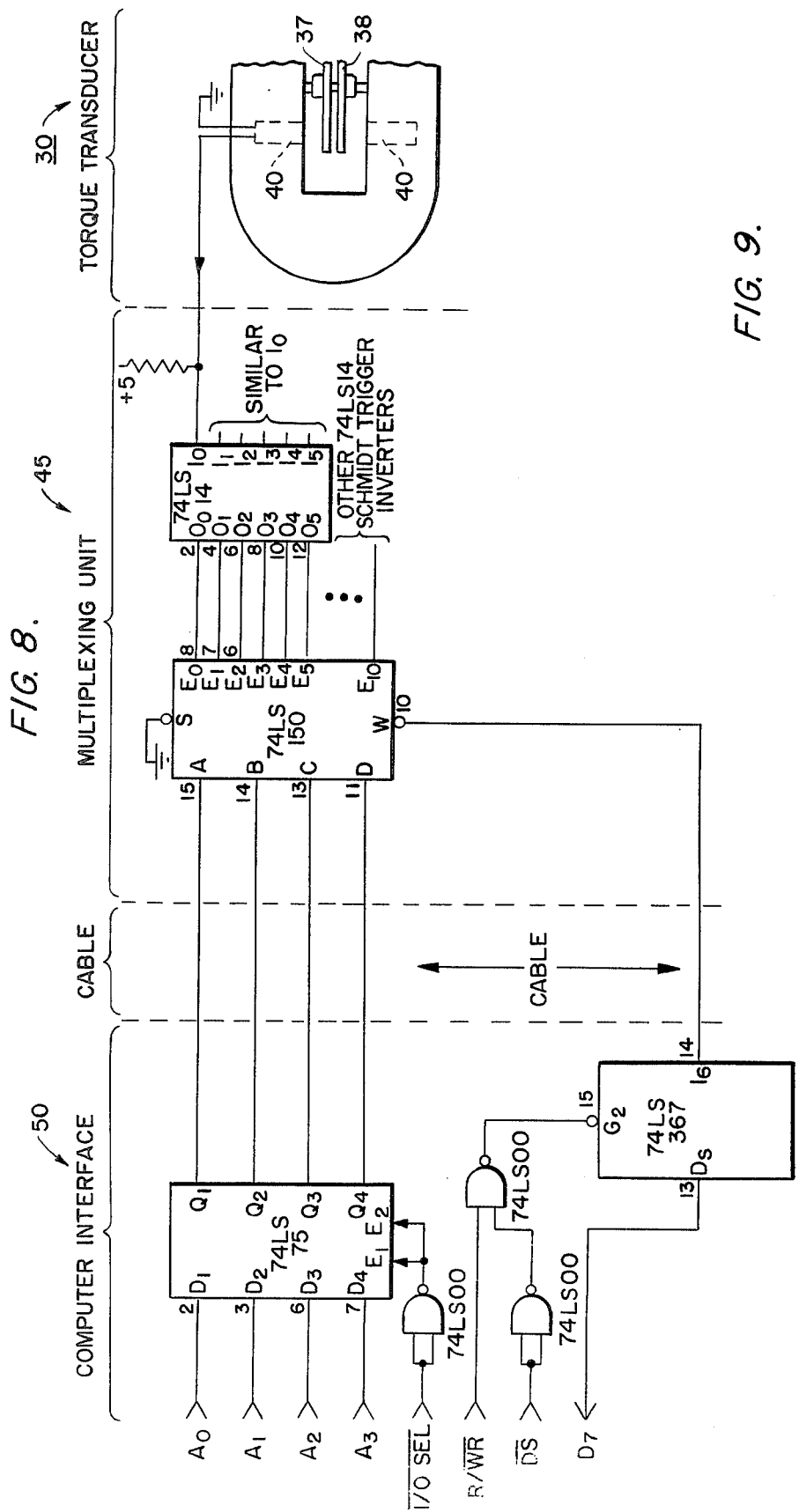

Referring to FIG. 1, which is a simplified showing of the overall deposit-build-up monitoring system 10, several major elements thereof can be identified. The annular fouling cell 20 comprises a region, indicated by a legend, through which fluid circulates. This fluid gradually fouls the facing surfaces of rotor 21 and cylindrical casing 22 by build-up of deposits, causing an increasing drag on the rotor shaft. The drag is a measure of the build-up, and is sensed by a torque transducer 30, which is located in the mechanical drive between drive motor 31 and rotor 21. The same drive motor 31 may drive rotors in other annular fouling cells, not shown, each having individual torque transducers, two of which, 30b and 30h are briefly indicated.

The electrical output from torque transducer 30 is indicative, by its frequency, of the rotation rate of the rotor 21, and by its duty cycle, of the torque required to drive rotor 21 at that rotation rate.

The electrical outputs of all the torque transducers are applied to a time division multiplexing unit 45, which takes the information from each torque transducer and, seriatim, feeds the corresponding individual pieces of information to the computer interface 50.

The computer interface 50 controls the sequencing of the multiplexing unit 45 by "polling" it, that is, by indicating to the multiplexing unit 45 which particular piece of information it wants at a particular time, at which time it accepts the information and feeds it to the microcomputer 60. In the prototype embodiment the well known "Apple II Plus" computer was used, but any other general use type computer may be used.

The computer 60 has a number of the customary peripherals, adapting the monitoring system for different purposes.

Low cost cassette storage 61 and high speed disk storage 62 are provided, permitting information or data to be retained and operated upon. A video monitor 63 is provided for visual read out of data and a printer 64 for hard-copy print-out out of data. An alarm 65 sounds if any of the data indicates an abnormal condition, such as excessive build-up or zero rotation rate for rotor 21. Finally, a time-sharing computer link 65, for manipulation and storage of data beyond the capacity of the low cost system illustrated, is provided.

The various portions of the deposit build-up monitoring system 10 of FIG. 1 are explained below, under headings, in greater detail.

Annular Fouling Cell

The construction of the annular fouling cell 20 is illustrated in FIGS. 2 through 4b. The rotor 21 rotates within cylindrical casing 22. Rotor 21 has four impeller blades 23 which are bridged by an impeller disk 24, and has four longitudinal draft tubes 25. It will be evident that, during rotation of rotor 21, the impellers 23 will act by centrifugal force to propel fluid rapidly outwardly. The propelled fluid then travels upwardly, between the rotor 21 and casing 22 to enter circulating fluid region 26. The draft tubes 25 draw fluid from region 26 to supply the flow to the impellers 23.

The fluid circulating region 26 is shown as a region with indefininite boundaries, partly to simplify the presentation. In practice, the annular fouling cell 20 would usually be separate from, say, the cooling tower with which is used, and would be connected to that tower by plastic tubing and a motor driven pump, not shown, to supply a sample of the cooling tower circulating water to inlet nipple 27. The excess circulating water would be returned to the cooling tower from outlet nipple 28. However, the annular fouling cell 20 could also be incorporated integrally into the cooling tower, and, in that case, could operate directly in the pool of cooling tower circulating water. A slide 29 is provided so that a sample of the deposit can be removed for observation of film thickness and density. Slide 29 fits flush into a shallow groove in the inner wall of casing 22, so that the radial annular spacing remains unchanged in the presence of the slide. Thus, growth of deposits is not ununiformly affected by localized variation in circulation. Slide 29 is seen in two views in FIGS. 4a and 4b, and needs no further explanation.

It will be noted that there are no concentration gradients in the fluid in the annular fouling cell 10 or in its sampling supply system, not illustrated, due to complete mixing. This simplifies mathematical description and sampling. Since the sample supply to inlet nipple 27 can be independently varied (as by varying the speed of the pump supplying the fluid sample) and since the speed of drive motor 31 can be independently varied, it follows that the mean residence time of fluid in annular fouling cell 20 can be varied independently of the fluid sheer stress in the annular space therein.

The following table presents relevant data about a prototype annular reactor which has been tested and found to be satisfactory:

| RELEVANT CHARACTERISTICS AND DIMENSIONS OF ANNULAR FOULING CELL | |
| --- | --- |
| Liquid Volume | 570 cm$^3$ |
| Total Wetted Surface Area (including draft tubes and impeller assembly) | 2000 cm$^2$ |
| Inner Cylinder Wetted Surface Area (including draft tubes and impeller assembly) | 1069 cm$^2$ |
| Outer Cylinder Wetted Surface Area | 931 cm$^2$ |
| Diamer of Inner Cylinder | 10.5 cm |
| Width of Annular Gap | 0.45 cm |
| Wetted Height of Inner Cylinder | 17.4 cm |
| Wetted Height of Outer Cylinder | 20.3 cm |
| Volumetric Flow Rate* (nutrients plus dilution water) | 57 cm$^3$/min |
| Mean Fluid Residence Time* | 10 min |
| Wetted Surface Area of removable slide | 60.9 cm$^2$ |
| Longitudinal dimension of slide | 22.5 cm |
| Face dimension of slide | 2.9 cm |

*Typical rate used with instant cell. Other rates available and useable.

Torque Transducer

The torque transducer 30 and its operation is described with the aid of FIGS. 5a, 5b, 6 and 7. The drive motor 31 of FIG. 1 is coupled to drive shaft 32, which is hollow in the region illustrated in FIG. 5a. Drive shaft 32 is supported by bearings 33, mounted in frame 34. Driven shaft 35, which turns rotor 21 of the annular fouling cell 20 is also hollow in the region illustrated and is supported by bearings 36 in such manner that the shafts 32 and 35 are in accurate alignment.

The two shafts 32 and 35 are connected together by torsion bar 39, which consists of a long thin easily twistable spindle having enlarged stub portions at each end. The two stubs respectively fit tightly into the hollows of shafts 32 and 35, and are firmly fixed to their respective said shafts, thereby connecting shafts. The fixing of the stub portions to their respective shafts 32 or 35 can be effected by cement, a low temperature braze, or by swaging or locally indenting the shaft. The torsion bar 39 will drive driven shaft 35 with the rotation of drive shaft 32, but the spindle portion of torsion bar will twist when the driven shaft 35 offers resistance to rotation. The amount of twist, which is a measure of the drag on driven shaft 35, is measured by upper and lower slotted disks 37 and 38, mounted respectively on drive and driven shafts 32 and 35, and optical sensing system 40.

The construction of the upper and lower slotted disks 37 and 38 is best seen in FIG. 6, where the lower disk 38 has been shown as slightly larger than the upper disk 37, so that the overlap of lower disk 38 by upper disk 37 will not hide any edges. It will be realized that in practice, the two disks would be constructed alike. From FIGS. 5a and 6 it will be evident that the optical sensing system 40 will be obstructed during most of the time when the disks are rotating, but that an angular window of varying width, depending on the torque being measured, will permit the optical sensing system 40 to be periodically unobstructed. The optical sensing system 40 consists of a light source on one side of the slotted disks 37 and 38 and a photocell on the other side thereof. The photocell current is in the form of a pulse train and is plotted as a function of time, in FIG. 7. This is an idealized plot which does not show the rounding of edges and noise found in real plots. The computer, to be described below, interprets this pulse train as torque and as rotational speed.

As the torque varies, the sector slot window opens and closes correspondingly, because the torsion bar 39 twists and untwists. This correspondingly varies the width of the pulse $t_1$, as seen in FIG. 7. As the speed varies, the repetition rate of the pulse train, $t_2$, correspondingly varies.

The following relations hold on this just described system:

$$t_1 = \theta/\Omega$$

$$t_2 = 360°/\Omega$$

where $\theta$ is the angular width in degrees of the "window" formed by the overlapping slots, and $\Omega$ is the rotational speed. $\theta$ is proportional to torque, $\tau$.

$$\theta = k\tau$$

$$t_1 = k\tau/\Omega$$

$$t_2 = 360°/\Omega$$

and the ratio $t_1/t_2$ is proportional to the torque alone:

$$t_1/t_2 = k\tau/360°$$

Thus, torque can be accurately measured over a wide range of rotational speeds. The constant, k, is determined by static measurement of $\theta$ and $\tau$ for a range of torques between 0 and 10 inch-ounces.

The constant k is stored in the computer, described below, and used to convert the pulse width data to torque.

A three-conductor cable, consisting of ground, +7.5 volts, and a signal line connects each torque transducer 30, 30b–30h (FIG. 1) to the multiplexing unit 45.

Multiplexing Unit

The Multiplexing Unit 45 allows the computer to select and monitor one of 16 torque transducers, and conditions incoming signals to give clean TTL logic level transitions. A schematic of the unit is shown in FIG. 8.

The 74LS14 Schmitt trigger-inverters accepts the relatively weak, erratic-pulse trains from the torque transducers and forms therefrom output pulses with well defined edges. These pulse trains are fed to the 74LS150 multiplexer which selects data to be transmitted to the computer. Selection is accomplished by decoding four latched address lines from the computer interface.

Computer Interface

The Computer Interface 50 consists of an address latch and an input data buffer.

The 74LS75 latch "remembers" the last torque transducer polled by the computer and transmits this address to the multiplexing unit.

The 74LS367 is a 3-state buffer which gates the pulse data onto the computer data buss when requested by computer software.

FIG. 9 is a table of bias voltages used in the circuitry of FIG. 8.

Computer Software

Figure 10:
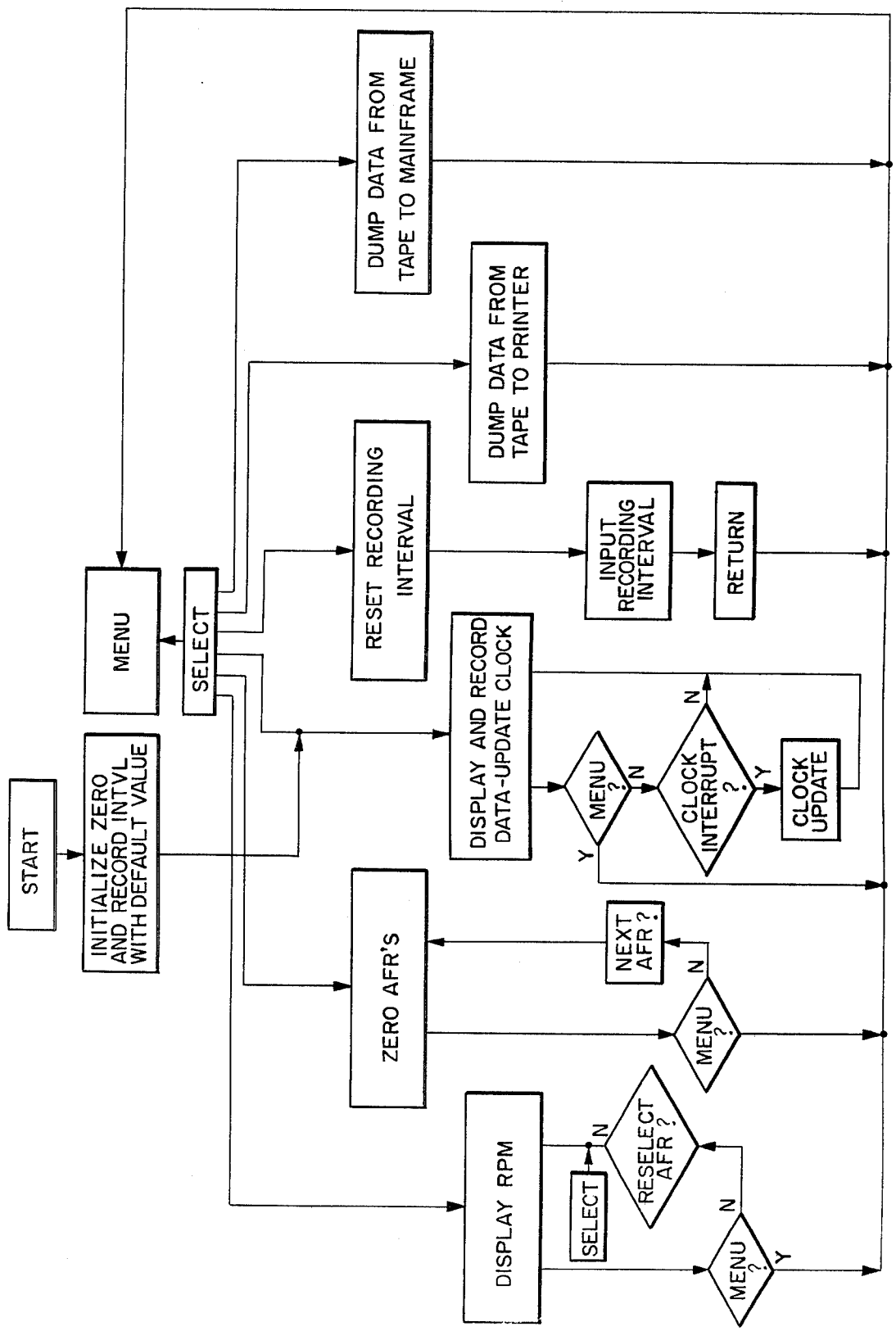
FIG. 10 is a flow diagram for the basic program.

Computer Software handles the bulk of data manipulation. The main program, which is interactive through keyboard input is written in basic. Machine language subroutines handle the monitoring of build-up of fouling and real-time clock interrupts. A flow diagram of the software is shown in FIG. 10 while a complete listing is contained in the appendix.

On power-up the program is entered into memory from disk and starts running.

The entry is by a procedure known as booting, in which a few instructions, initially loaded, control further loading of the entire routine.

Figure 11:
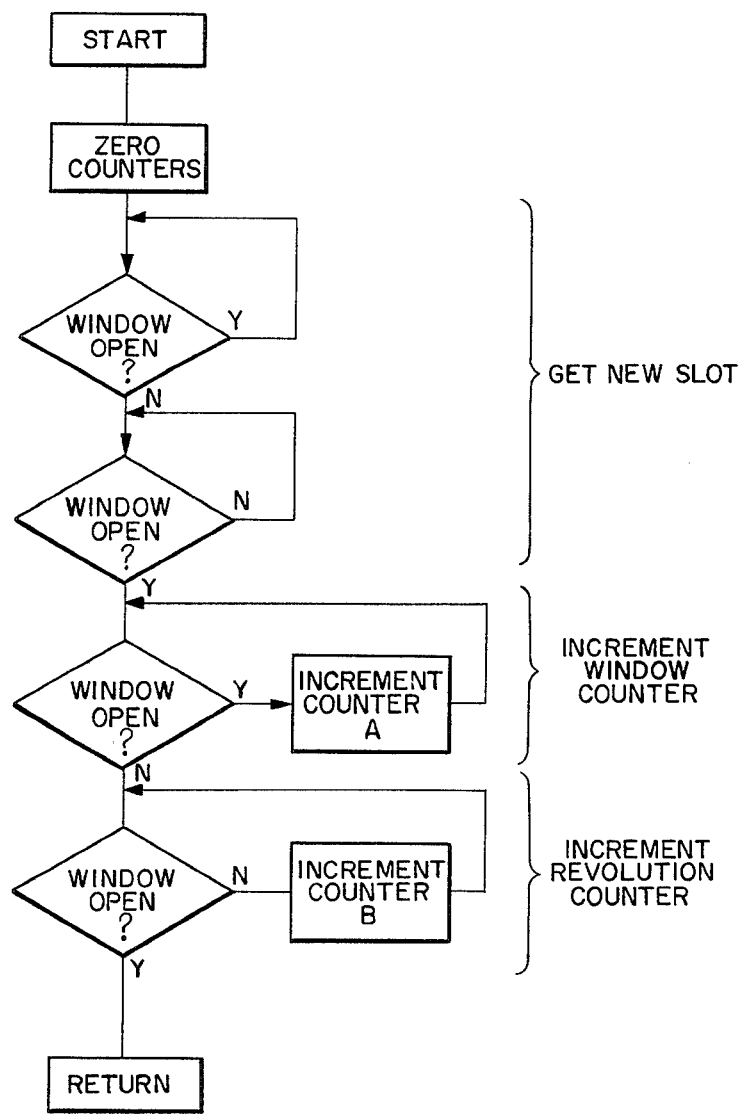
FIG. 11 is a flow diagram for the machine language subroutine used to monitor status of the torque transducer window.

A machine language subroutine, as diagramed in FIG. 11, is called on to measure the pulse rate and pulse width generated by the variable gap "window" from a single torque transducer. This is accomplished by rapidly looping through a program which scans the memory location assigned to the "window" and senses its status. When a fresh "open" status or set condition is sensed, a counter starts incrementing. When a fresh "closed" status is sensed a second counter starts incrementing. When a new "open" status is sensed the subroutine returns control to the Basic Program.

The value left in the open status counter is then divided by the sum of the values in the open status counter and closed status counter and multiplied by a calibration factor stored in memory to obtain torque. The sum of the values in the open and closed status counters is multiplied by a second factor to obtain RPM. A zero torque value, either set by default at power-up, or determined experimentally at the beginning of the experiment, is subtracted from the current value to obtain actual torque.

A menu of subprogram options may be called up at any time by pressing the "escape" key. These include:
(1) Instantaneous RPM display for single annular fouling cells.
(2) Automatic zeroing of individual annular fouling cells.
(3) The main monitoring, display, and data recording program.
(4) Resetting data recording interval.
(5) Dump data from tape to printer.
(6) Dump data from tape to central computer.

Clock Interrupt System

Run time display and data recording are controlled by a clock interrupt system. A hardware schematic for the clock is shown in FIG. 12. It consists of a signal conditioner which converts the 60 hertz line signal into 60 hertz TTL logic level pulses with well defined edges, and a frequency divider chain. Finally, a one-shot multivibrator insures that a pulse of approximately 1 msec duration is applied to the interrupt line of the Apple Computer. The clock can be switched to interrupt every second, minute, or every 4 minutes.

The clock interrupt servicing routine sets a flag which is periodically checked and reset by the basic program. A time-update subroutine is called if a set flag is encountered.

The main program displays the current time and checks the recording interval value to see if it is time to save data.

Unlike some computers, the Apple does not automatically start the recorder when it writes to tape. An interface was constructed which accomplishes this. A schematic is shown in FIG. 14. The 311 comparator senses the low level train of sync pulses first transmitted by the Apple. It amplifies these to about +5 V. The 555 timer serves as a retriggerable monostable multivibrator with a pulse width of about one second. As long as the Apple sends data to the recorder, the 555 is on. When data transmission ceases, there is a one second delay before the 555 turns off. The 555 activates a reed relay which is connected to the "Remote" input of the cassette recorder. Thus, whenever information is being transmitted to the tape recorder, the recorder is turned on via the "Remote" switch.

Data is stored as a two dimensional array with the cell number as the first dimension and the measured variable as the second dimension. The measured variables are:
(1) Identification number of annular fouling cell
(2) RPM
(3) Average Torque
(4) Standard deviation of the average torque
(5) Time This amount of data requires an 8 by 5 or 40 element array in storage.

Operation

To operate the system, the following procedures should be followed:
(1) Set sample water flow rate.
(2) Switch variable speed motor on and set rotational direction to "reverse".
(3) Make sure overflow is high enough to completely fill the annular fouling cell.
(4) Insert blank audio tape in recorder, set to record, and set recorder interface to "Auto".
(5) Insert annular fouling cell monitor disk into disk drive and close door.
(6) Turn on Apple Computer-the monitor screen format should appear, and RPM and torque data soon after that.
(7) Push "ESC" key to call menu.
(8) Select RPM display.

(9) Set each pair of annular fouling cells to optimal RPM by adjusting the speed of variable speed motor 31 while watching RPM display. Since two annular fouling cells are driven by a single motor, the speeds will probably be only approximate.
(10) Return to the menu.
(11) Select torque monitor zeroing.
(12) Select experimental zeroing.
(13) Zero each torque monitor.
(14) Return to the menu and then to "Measure, Display, and Record".
(15) The RPM indications should all be reasonably close to desired set values and the torques should be close to zero with a very low (0.2) standard deviation.
(16) Allow zero time data to be recorded. This should occur within one minute.
(17) If a recording interval of other than 60 minutes is required, return to the menu and select recording interval change.
(18) Return to "Measure, Display, Record".

Appendix

```
JLIST
10   HIMEM: 8191: REM  END OF BASIC SPACE AT HEX 1FFF
20   REM  INTERFACE IN SLOT #2
30   REM  INSERT MACHINE LANGUAGE SUBROUTINES AT HEX 2010-206F
40   RESTORE
50   DATA 160,192,80,251,44,169,0,160,5,153,0,32,136,16,250,44,160,192,16,251,44,
         160,192,48,251,162,0,32,62,32,44,160,192,16,248,162,2,32,62
60   DATA 32,44,160,192,48,248,96,234,234,234,234,234,254,0,32,240,7,234,234,234,
         234,234,234,96,232,254,0,32,240,1,96,142,4,32,96,234,234,104,168
70   DATA 104,162,252,154,72,152,72,96,88,96,120,96,0,72,169,1,141,101,32,104,
         165,69,64,223
80   FOR N = 8203 TO 8304
90   READ HX: POKE N,HX
100  NEXT N
110  POKE 1022,102: POKE 1023,32: REM  CLOCK INTERRUPT
120  REM         MAIN PROGRAM
130  DIM QCAL(16),QZERO(16),A(8,5),TACH(16)
140  REM SET DEFAULT VALUES FOR QCAL QZERO AND TACH
150  DATA 19.98,19.80,19.81,19.69,19.78,19.75,20.00,19.74,236587,230637,245213,
         254364,238692,261420,225120,228259
160  FOR N = 1 TO 8
170  READ QCAL:QCAL(N) = QCAL:QZERO(N) = 6.00
180  NEXT
190  FOR N = 1 TO 8: READ TACH(N): NEXT
200  REM  KEYBOARD INPUT FOR TIME AND AFR SELECTION
210  HOME : PRINT " ENTER DATE AND TIME (E.G. 8/21/81-1638 WOULD BE 0821811638)"
220  INPUT KEG
230  ITVL = 60:MIN = 0:HRS = 0:TIME = 0
240  GOTO 1300
250  REM  MASTER MENU
260  HOME : VTAB 8: PRINT "--------- AFR MONITOR MENU ---------"
270  CALL 8279
280  PRINT : PRINT "    1) DISPLAY RPM"
290  PRINT "    2) ZERO TORQUE MONITORS"
300  PRINT "    3) MEASURE, DISPLAY, RECORD"
310  PRINT "       RPM, TORQUE, TEMP, TIME"
320  PRINT "    4) SET RECORDING INTERVAL"
330  PRINT "    5) WHICH AFRS OPERATING"
340  GOSUB 1070: IF Y = 155 THEN GOTO 340
350  ON Y GOTO 380,470,670,960,1300,260,260,260
360  GOTO 340
370  REM DISPLAY RPM ONLY
380  HOME : VTAB 10: PRINT "WHICH AFR RPM DO YOU WANT DISPLAYED ?"
390  GOSUB 1070
400  IF ASELECT(AFR) = 0 THEN  GOTO 380
410  POKE 49663 + AFR,0
420  GOSUB 1180
430  RPM = INT (TACH(AFR) / REV)
440  VTAB 13: PRINT "RPM FOR AFR #";AFR;" = ";: CALL - 868: PRINT RPM
450  GOTO 390
```

```
460  REM   ZERO AFR'S
470  HOME : VTAB 10: PRINT "SET ZERO EXPERIMENTALLY (1) OR BY KEYBOARD INPUT (2)?"
480  AFR = 0: GOSUB 1070
490  IF AFR = 1 THEN  GOTO 520
500  IF AFR = 2 THEN  GOTO 630
510  GOTO 480
520  HOME : VTAB 10: PRINT "IF RPM HAS BEEN SET, WHICH AFR NEEDS ZEROING ?"
530  AFR = 0: GOSUB 1070
540  IF AFR = 0 OR ASELECT(AFR) = 0 THEN  GOTO 530
550  VTAB 6: PRINT "ZEROING AFR #";AFR
560  POKE 49663 + AFR,0
570  TOTR = 0
580  FOR N = 0 TO 19: GOSUB 1180
590  TOTR = TOTR + RTIO: NEXT
600  QZERO(AFR) = TOTR / 20 + QCAL(AFR)
610  VTAB 15: PRINT QZERO(AFR)
620  VTAB 6: CALL  - 868: PRINT "NEXT?": GOTO 530
630  HOME : VTAB 10: INPUT "ENTER 'AFR','ZERO' (ENTER '0' AFR TO EXIT)";V,QZERO(V)
640  IF V <  > 0 THEN  GOTO 630
650  GOSUB 1070
660  GOTO 650
670  REM    MONITOR PROGRAM
680  HOME
690  VTAB 3: PRINT "          ------AFR MONITOR------- ": PRINT
700  PRINT "          RUNTIME:"
710  PRINT : PRINT "AFR:";"RPM","TORQUE","FF"
720  FOR AFR = 1 TO 8
730  IF ASELECT(AFR) = 0 THEN  GOTO 920
740  POKE 49663 + AFR,0
750  AVG = 0:STD = 0:RPM = 0:TEMP = 0
760  FOR N = 0 TO 9
770  GOSUB 1070
780  GOSUB 1180
790  IF  PEEK (8293) = 1 THEN  POKE 8293,0: GOSUB 990
800  RTIO = QCAL(AFR) + RTIO - QZERO(AFR)
810  AVG = AVG - RTIO
820  STD = STD + RTIO ^ 2
830  RPM = RPM + TACH(AFR) / REV
840  NEXT
850  STD =  SQR (STD / 10 - AVG ^ 2 / 100):STD =  INT (STD * 100 + .5) / 100
860  AVG = AVG / 10:AVG =  INT (AVG * 100 + .5) / 100
870  RPM =  INT (RPM / 10)
880  IF RPM = 0 THEN  GOTO 900
890  FF = 36.90 * AVG / RPM ^ 2:FF =  INT (FF * 1000 + .5) / 1000
900  A(AFR,0) = REG:A(AFR,1) = HRS + MIN / 60:A(AFR,2) = RPM:A(AFR,3) =
        AVG:A(AFR,4) = STD:A(AFR,5) = FF
910  VTAB 8 + AFR: CALL  - 868: PRINT AFR;":";RPM,AVG;"(";STD;")    ";FF
920  NEXT
930  CALL 8289
940  GOTO 720
950  REM   SET RECORDING INTERVAL
960  HOME : INPUT "WHAT RECORDING INTERVAL DO YOU WANT ( ENTER AS MINUTES )";ITVL
970  GOSUB 1070: GOTO 970
980  REM UPDATE TIME AND STORE DATA ON TAPE
990  CALL 8291: IF TIME = 0 THEN  POKE 49241,0: STORE A: POKE 49240,0
1000 TIME = TIME + 1
1010 IF TIME >  = ITVL THEN TIME = 0
1020 VTAB 5: HTAB 20: CALL  - 868: PRINT HRS;":";MIN
1030 MIN = MIN + 1
1040 IF MIN = 60 THEN MIN = 0:HRS = HRS + 1
1050 CALL 8289
```

```
1060  RETURN
1070  REM    AFR KEYBOARD PROCESSOR
1080  VTAB 21: PRINT "TO EXIT PRESS 'ESC' KEY"
1090  Y = PEEK (49152): POKE 49168,0
1100  IF Y < 128 THEN  RETURN
1110  IF Y = 155 THEN  GOSUB 1170: GOTO 260
1120  Y = Y - 176
1130  FOR N = 1 TO 8
1140  IF Y = N THEN  GOSUB 1170:AFR = N: RETURN
1150  NEXT
1160  VTAB 20: PRINT "WRONG KEY - TRY AGAIN!": GOTO 1090
1170  VTAB 20: CALL  - 868: RETURN
1180  REM      MACHINE LANGUAGE SUBROUTINE INTERFACE
1190  CALL 8208
1200  SLOT =  PEEK (8193) * 256 +  PEEK (8192)
1210  MASK =  PEEK (8195) * 256 +  PEEK (8194)
1220  REV = SLOT + MASK:RTIO = SLOT / REV
1230  OVRANGE =  PEEK (8196)
1240  RETURN
1250  GOSUB 1070
1260  PRINT Y,AFR: GOTO 1250
1270  CALL 8279
1280  PRINT N
1290  GOTO 1250
1300  REM   SELECT AFRS TO RUN
1310  HOME : PRINT "AFR SELECTION": PRINT : PRINT
1320  FOR N = 1 TO 8
1330  VTAB 10: PRINT "AFR #";N;" (Y/N)";
1340  INPUT A$
1350  ASELECT(N) = 0: IF A$ = "Y" THEN ASELECT(N) = 1
1360  NEXT
1370  GOTO 260
```

Machine Language Subroutines

```
2010- A9 00 A0 05 99 00 20 88
*2010LLL

2010-   A9 00       LDA    #$00
2012-   A0 05       LDY    #$05
2014-   99 00 20    STA    $2000,Y
2017-   88          DEY
2018-   10 FA       BPL    $2014
201A-   2C A0 C0    BIT    $C0A0
201D-   10 FB       BPL    $201A
201F-   2C A0 C0    BIT    $C0A0
2022-   30 FB       BMI    $201F
2024-   A2 00       LDX    #$00
2026-   20 3E 20    JSR    $203E
2029-   2C A0 C0    BIT    $C0A0
202C-   10 F8       BPL    $2026
202E-   A2 02       LDX    #$02
2030-   20 3E 20    JSR    $203E
2033-   2C A0 C0    BIT    $C0A0
2036-   30 F8       BMI    $2030
2038-   60          RTS
2039-   EA          NOP
203A-   EA          NOP
203B-   EA          NOP
203C-   EA          NOP
203D-   EA          NOP
```

```
203E-   FE 00 20    INC   $2000,X
2041-   F0 07       BEQ   $204A
2043-   EA          NOP
2044-   EA          NOP
2045-   EA          NOP
2046-   EA          NOP
2047-   EA          NOP
2048-   EA          NOP
2049-   60          RTS
204A-   E8          INX
204B-   FE 00 20    INC   $2000,X
204E-   F0 01       BEQ   $2051
2050-   60          RTS
2051-   8E 04 20    STX   $2004
2054-   60          RTS
2055-   EA          NOP
2056-   EA          NOP
2057-   68          PLA
2058-   A8          TAY
2059-   68          PLA
205A-   A2 FC       LDX   #$FC
205C-   9A          TXS
205D-   48          PHA
205E-   98          TYA
205F-   48          PHA
2060-   60          RTS
2061-   58          CLI
2062-   60          RTS
2063-   78          SEI
2064-   60          RTS
2065-   00          BRK
2066-   48          PHA
2067-   A9 01       LDA   #$01
2069-   8D 65 20    STA   $2065
206C-   68          PLA
206D-   A5 45       LDA   $45
206F-   40          RTI
```

We claim:

1. An instrument for monitoring the build-up of fouling deposits on the fluid-contacting surfaces of fluid handling systems comprising, in combination:

a fouling cell having a cylindrical rotor adapted for rotation on its axis within an annular cylindrical casing;

means to flow fluid from the fluid handling system under investigation through the said fouling cell;

means to rotate said rotor at a selected rotational speed, thereby inducing a corresponding sheering stress in the fluid under investigation;

said means to flow fluid being supported by and rotating with said cylindrical rotor and comprising, further, means to cause the fluid to flow longitudinally along the annular space between said cylindrical rotor and said annular cylindrical casing;

means to sense the actual rotational speed of said rotor and to sense the torque required to drive said rotor said actual rotational speed and to emit corresponding electrical signals in response to the sensing;

means to feed said emitted signal to a computer for decoding said signals into machine-language signals representing the actual rotational speed and torque sensed;

means, including program means, in said computer for manipulating said machine language signals to supply and display information as to the actual rotational speed and the torque required.

2. The subject matter of claim 1 in which:

said means to flow fluid comprises longitudinal fluid circulating channels and radial impeller blades which, through the rotation of the rotor and the action of centrifugal force, permit and propel the fluid to circulate longitudinally in the annular space between the cylindrical rotor and the annular cylindrical casing.

3. The subject matter of claim 1 in which:

the fouling cell comprises a sample test slide, said test slide being retained, during use, in a groove in said annular cylindrical casing;

said slide and said groove having cooperating shapes, so that said slide, when retained in said groove, presents only an exterior face to said annular space, said exterior face being a faired continuation of said annular cylindrical casing;

whereby the said annular space is not changed by the presence of said slide; and whereby no local ununiformity of circulation is produced by presence of said slide.

4. The subject matter of claim 1 in which:

the means to sense the actual rotation speed of the cylindrical rotor and the torque required to drive it comprises a twistable torsion bar in the mechanical drive between the means to rotate the cylindrical rotor and the cylindrical rotor;

two sector disks respectively mounted to rotate with said torsion bar at opposite ends thereof;

said sectors being so arranged as to variably overlap as said torsion bar twists and untwists in response to varying torque; and a stationary optical sensing system responsive to the passing of the sectors in said two sector disks, for producing one electrical signal when both sectors are open to said stationary optical sensing system and for producing a different electrical signal when either or both of said sector disks obturate said stationary optical sensing system.

5. The subject matter of claim 4 in which:

said computer responds to the beginning and termination of said one and said different electrical signals and counts increments of time during which said one electrical signal occurs, to reach one total count, and counts increments of time during which said different electrical signal occurs, to reach a different total count;

said computer deriving the rotational speed as the product of a constant and the sum of said one total count and said different total count during one complete cycle of said beginning and termination; and said computer deriving the torque as the product of a different constant times the ratio of said one total count to the sum of said one total count and said different total count.

* * * * *